United States Patent [19]

Arndt et al.

[11] 4,072,497
[45] Feb. 7, 1978

[54] (5-ALKYLUREIDO-1,3,4-THIADIAZOL-2-YL-THIO) ACETIC ACID TERT-BUTYL ESTERS AND HERBICIDAL COMPOSITIONS AND PROCESSES

[75] Inventors: Friedrich Arndt; Ludwig Nüsslein, both of Berlin, Germany

[73] Assignee: Schering Aktiengesellschaft, Berlin and Bergkamen, Germany

[21] Appl. No.: 759,560

[22] Filed: Jan. 14, 1977

[30] Foreign Application Priority Data

Jan. 16, 1976 Germany .............................. 2601987

[51] Int. Cl.$^2$ ...................... A01N 9/12; C07D 285/12
[52] U.S. Cl. .................................. 71/90; 260/306.8 D
[58] Field of Search ..................... 260/306.8 D; 71/90

[56] References Cited

FOREIGN PATENT DOCUMENTS 743,615  6/1970  Belgium .......................... 260/306.8 D Primary Examiner—R. Gallagher
Attorney, Agent, or Firm—Michael J. Striker

[57] ABSTRACT

[5-(1,3-dimethylureido)-1,3,4-thiadiazol-2-ylthio]-acetic acid methylester (b.p. 113° C), [5-(1,3,3-trimethylureido)-1,3,4-thiadiazol-2-ylthio]-acetic acid ethylester (b.p. 95° C) and [5-(3-methylureido)-1,3,4-thiadiazol-2-ylthio]-acetic acid isopropylester (b.p. 143° C) in which R is hydrogen or alkyl. The compounds are useful as the active agents or one of the active agents in herbicidal compositions.

6 Claims, No Drawings

(5-ALKYLUREIDO-1,3,4-THIADIAZOL-2-YL-THIO) ACETIC ACID TERT-BUTYL ESTERS AND HERBICIDAL COMPOSITIONS AND PROCESSES

BACKGROUND OF THE INVENTION

The invention relates to (5-alkylureido-1,3,4-thiadiazol-2-yl-thio) acetic acid esters. (5-alkylureido-1,3,4-thiadiazol-2-yl-thio)-carboxylic acid esters have already been proposed in general form for use as herbicidal agents (West-German Pat. No. 1,817,949) without, however, identifying specific active agents. Subsequent tests have shown that for instance [5-(1,3-dimethylureido)-1,3,4-thiadiazol-2-ylthio]-acetic acid ethylester (b.p. 113° C), [5-(1,3,3-trimethylureido)-1,3,4-thiadiazol-2-ylthio]-acetic acid ethylester (b.p. 95° C) and [5-(3-methylureido)-1,3,4-thiadiazol-2-ylthio]-acetic acid isopropylester (b.p. 143° C) has no herbicidal activity.

SUMMARY OF THE INVENTION

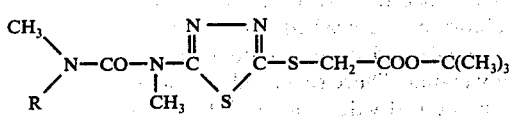

in which R is hydrogen or alkyl. The compounds have an excellent herbicidal action and can therefore be used as weed-killing agents.

This herbicidal action was particularly surprising and could not be predicted since analogous compounds as shown above do not have a similar action.

DISCUSSION OF THE INVENTION AND SPECIFIC EMBODIMENTS

The compounds of the invention can for instance be employed as herbicides with an overall activity for destroying a wasteland flora and destroying entire bushes or they can be used as selective herbicides for agricultural crops. They are suited for instance for suppressing monocotyloyd weeds such as Poa, *Eleusine indica*, Setaria, Echinochloa, Digitaria, *Avena fatua*, Alopecurus and *Sorghum halepense*; of dicotyloid weeds, such as Stellaria, Senecio, Matricaria, Lamium, Centaurea, Amaranthus, Galium, Chrysanthemum, Ipomea, Polygonum and Xanthium.

As agricultural crops in which the compounds of the invention are useful there may be mentioned oats, barley, wheat, rice, maize, peanuts, peas and potatoes.

In addition to their wide spectrum of action and high selectivity the compounds are useful against weed grasses, in particular millet grasses which on the basis of the present art are very difficult to suppress. The compounds of the invention are distinguished in this respect by a superior activity as compared with compounds having activities pointing in a similar direction.

As herbicides against seed weeds there are usually comparatively small amounts necessary of about 0.4 to 1.5 kg of active agent per about 2.5 acres of land.

The compounds of the invention can be used either by themselves, intermixed with each other or in mixture with other active agents. Depending on the desired purpose there may be used other defoliants, plant protection agents or pest control agents with them. If a further broadening of the activity spectrum is intended other herbicides may be used along with the compounds of the invention.

An increase in the intensity of the action and/or the speed of action can for instance be obtained by action increasing additives such as additions of organic solvents, cross-linking agents and oils which then would result in a reduction of the amount necessary of the compounds of the invention or of mixtures of these compounds or of mixtures with other active agents.

The compounds of the invention or their mixtures are preferably used in compositions in the form of powders, dusting agents, granulates, solutions, emulsions or suspensions to which may be added liquid and/or solid carrier materials or diluents or, if desired, agents which aid the cross-linking, adhesion, emulsion and/or dispersion effect.

Suitable liquid carrier materials are, for instance, water, aliphatic and aromatic hydrocarbons such as benzene, toluene, xylene, cyclohexanone, isophorone, dimethylsulfoxide, dimethylformamide, and furthermore mineral oil fractions.

As solid carriers there may be used minerals and earths, such as tonsil, silica gel, talc, kaolin, atta purgite clay, limestone, silicic acid and plant products, e.g. flours.

Suitable surface active agents are e.g. a calcium-ligno sulfonate, polyoxyethylene alkylphenyl ether, naphthaline sulfone acids and their salts, phenolsulfone acids and their salts. formaldehyde condensates, fatty alcohol sulfates and substituted benzosulfone acids and their salts.

The contents of the active agent or agents in the different compositions can be varied widely. The compositions for instance may contain about 10 to 80% by weight of active agents, about 90 to 20% by weight of liquid or solid carrier materials and, if desired, up to 20% by weight of surface active agents. The application of the compositions can be effected in conventional manner for instance with water as carrier material in total spray amounts of about 100 to 1000 liter per about 2.5 acres. The application of the compositions is possible in the so-called "low volume" and so-called "ultra-low-volume process" as also in the form of so-called microgranulates.

Process of Making

The compounds of the invention can be made for instance by reacting

A. (5-methylamino-1,3,4-thiadiazol-2-yl-thio)-acetic acid tert. butylester of the formula

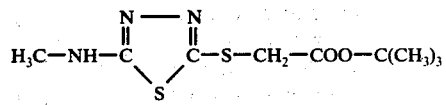

with any of the following:
(a) carbamoylchloride of the formula

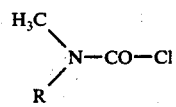

(b) phosgene and amines of the formulae

and

(c) carbamic acid esters of the formula

or (d) if R in the final product is intended to be H, with methylisocyanate of the formula CH₃—NCO.

The reaction may be carried out in a solvent or in the presence of an acid acceptor.

Another way of making the compounds of the invention would be the following:

B. Reacting a carbamic acid ester of the formula

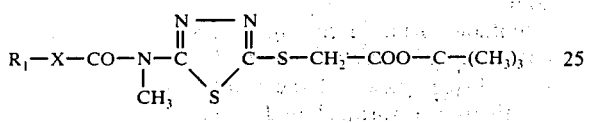

with an alkylamine of the formula

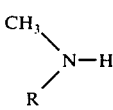

In all these formulae R is hydrogen or alkyl, R₁ is alkyl or phenol and X is oxygen or sulfur.

The starting products for making the compounds of the invention are known and can be made by conventional processes. In processes where hydrochloric acid is formed it is preferred to use an acid acceptor such as organic bases, like tertiary amines, for instance triethylamine, N,N-dimethylaniline or pyridine bases. There may also be used inorganic bases such as oxides, hydroxides or carbonates of the alkali-and earthalkali metals.

The reaction of the components may be effected at a temperature between about −20° and 100° C, preferably, however, at room temperature.

For carrying out the reactions the components are used in about equimolar amounts.

Suitable reaction media are solvents which are inert to the components. As examples there are mentioned: aliphatic and aromatic hydrocarbons such as petroleum, ethers, cyclohexane, benzene, toluene and xylene, halogenated hydrocarbons such as, methylene chloride, chloroform, carbon tetrachloride and halogenated ethylenes, ether type compounds such as diethylether, diisopropylether, tetrahydrofuran and dioxane, ketones such as acetone, methylisobutylketone and isophorone, esters, such as acetic acid methyl- and -ethylester, acid amides, such as dimethyl formamide and hexamethylphosphoric acid triamide, carboxylic acid nitriles, such as acetonitrile and others.

EXAMPLES

The following Examples will further illustrate the invention.

EXAMPLE A

[5-(1,3,3-trimethylureido)-1,3,4-thiadiazol-2-ylthio]-acetic acid tert. butylester 25 ml of phosgene were condensed at −20° C and were dissolved in 50 ml of methylene chloride. At −5° to 0° C a solution of 67 g of (5-methylamino-1,3,4-thiadiazol-2-ylthio)-acetic acid tert. butylester and 33 ml N,N-dimethylaniline in 400 ml methylene chloride were added dropwise during a period of 30 minutes while stirring and applying external cooling. The addition was affected dropwise. After 2 hours further stirring, the reaction mixture was stirred into ice-water, the organic phase was separated, dried on magnesium sulfate and concentrated in a vacuum. The oily residue was taken up in 100 ml acetonitrile and was added dropwise while stirring at 10° C to a mixture consisting of 18.76 g dimethylamine hydrochloride, 64.11 ml triethylamine and 250 ml acetonitrile.

The reaction mixture was then further stirred for 1 hour, was added to ice-water, was extracted with methylene chloride, and washed with water. The extraction medium was dried on magnesium sulfate and distilled off in a vacuum. There remained as residue 68 g (79.8% of the theoretical value) of an oil having the refraction index $n_D^{20}$: 1.5549 which crystallized after a while. The melting point of the [5-(1,3,3-trimethylureido)-1,3,4-thiadiazol-2-ylthio]-acetic acid-tert.-butylester was 76° to 78° C.

EXAMPLE B

[5-(1,3-dimethylureido)-1,3,4-thiadiazol-2-ylthio]-acetic acid tert.-butylester 31.2 g of (5-methylamino-1,3,4-thiadiazol-2-ylthio)-acetic acid tert. butylester were dissolved in 100 ml tetrahydrofuran and were reacted dropwise while stirring with 7.2 ml methylisocyanate. After standing for several hours the precipitated mass was removed by suction, washed with diisopropyl ether and dried. There were obtained 15.0 g (39.5% of the theoretical value) of [5-(1,3-dimethylureido)-1,3,4-thiadiazol-2-ylthio]-acetic acid tert. butylester having a melting point of 174° C.

The compounds of the invention are colorless and non-smelling; they are in the form of crystalline compounds which are only little soluble in water but well soluble in organic solvents such as hydrocarbons, halogenated hydrocarbons, ethers, ketones, alcohols, carboxylic acids, esters, carboxylic acid amides and carboxylic acid nitriles.

USE OF THE COMPOUNDS

The herbicidal action of the compounds of the invention appears from the following test examples.

EXAMPLES 1

In a hothouse there were treated the following plants in a preemergence application with the listed compounds in an amount of 1 kg active agent per about 2.5 acres. The agent for this purpose was uniformly applied to the ground as an aqueous suspension in an amount of 500 liters per about 2.5 acres. The results after 3 weeks following the application showed that the activity of the compounds of the invention was better and their selectivity was higher than the control compounds as appears from the following Test Table.

TABLE I

| Compound of the Invention | Pea-nut | Echino-chloa | Sorghum hale-pense | Set-aria | Digit-aria | Poa | Alopec-urus | Avena | Galium |
|---|---|---|---|---|---|---|---|---|---|
| [5-(1,3,3-trimethylureido)-1,3,4-thiadiazol-2-ylthio]-acetic acid tert. butylester | 10 | 0 | 0 | 0 | 0 | 0 | 0 | 0 | 0 |
| Control compounds | | | | | | | | | |
| 1,1,3-trimethyl-3-(5-n-butyl-sulfonyl-1,3,4-thiadiazol-2-yl) urea | 8 | 5 | 4 | 1 | 5 | 0 | 2 | 6 | 2 |
| [5-(1,3-dimethylureido)-1,3,4-thiadiazol-2-ylthio]-acetic acid methylester | 10 | 10 | 10 | 10 | 10 | 10 | 10 | 10 | 10 |
| [5-(1,3,3-trimethylureido)-1,3,4-thiadiazol-2-ylthio]-acetic acid ethylester | 10 | 10 | 10 | 10 | 10 | 10 | 10 | 10 | 10 |
| [5-(3-methylureido)-1,3,4-thiadiazol-2-ylthio]-acetic acid isopropylester | 10 | 10 | 10 | 10 | 10 | 10 | 10 | 10 | 10 |

0 = total destruction
10 = unharmed

EXAMPLE 2

The plants shown in Table II were treated in a hot house in a postemergence application with the listed compounds in an amount of 1 kg active agent per about 2.5 acres. The compositions were applied by uniform spraying of the plants with an aqueous suspension in an amount of 500 l per about 2.5 acres.

Three weeks after application it was found also in this case that the compounds of the invention had a higher activity and better selectivity than the comparison compounds.

TABLE II

| Compound of the Invention | Pea-nut | Echino-chloa | Sorghum hale-pense | Set-aria | Digi-taria | Poa | Alope-curus | Avena | Galium |
|---|---|---|---|---|---|---|---|---|---|
| [5-(1,3,3-trimethylureido)-1,3,4-thiadiazol-2-ylthio]-acetic acid tert. butylester | 10 | 0 | 0 | 0 | 0 | 0 | 0 | 0 | 0 |
| Control compounds | | | | | | | | | |
| 1,1,3-trimethyl-3-(5-n-butyl-sulfonyl-1,3,4-thiadiazol-2-yl)-urea | 5 | 2 | 3 | 0 | 4 | 0 | 2 | 0 | 0 |
| [5-(1,3-dimethylureido)-1,3,4-thiadiazol-2-ylthio]-acetic acid methylester | 10 | 10 | 10 | 10 | 10 | 10 | 10 | 10 | 10 |
| [5-(1,3,3-trimethylureido)-1,3,4-thiadiazol-2-ylthio]-acetic acid ethylester | 10 | 10 | 10 | 10 | 10 | 10 | 10 | 10 | 10 |
| [5-(3-methylureido)-1,3,4-thiadiazol-2-ylthio]-acetic acid isopropylester | 10 | 10 | 10 | 10 | 10 | 10 | 10 | 10 | 10 |

0 = total destruction
10 = unharmed

In the above tests the area of land treated was in each case 1 hectar according to the metric system which corresponds to about 2.5 acres and was accordingly stated in the above description.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. (5-alkylureido-1,3,4-thiadiazol-2-yl-thio)-acetic acid ester of the formula

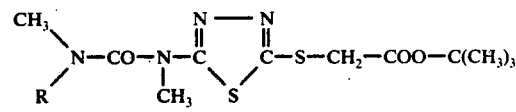

wherein R is hydrogen or methyl.

2. [5-(1,3,3-trimethylureido)-1,3,4-thiadiazol-2-ylthio]-acetic acid tert. butylester.

3. [5-(1,3-dimethylureido)-1,3,4-thiadiazol-2-ylthio]-acetic acid tert. butylester.

4. A herbicidal composition comprising from about 10 to 80% by weight of one or more of the esters defined in claim 1 and from about 90 to 20% by weight of a liquid or solid carrier material or a mixture of liquid and solid carrier materials.

5. A herbicidal composition as defined in claim 4 which additionally includes 20% by weight of a surface active agent or a plurality of such agents with a corresponding reduction of the other components.

6. A process of applying the composition of claim 4 to agricultural land for destruction, inhibition or reduction of undesirable weeds, comprising applying the said composition in an amount to provide for about 0.4 to 1.5 kg of active agents per about 2.5 acres of land.

* * * * *